(12) United States Patent
Clark

(10) Patent No.: US 6,349,720 B1
(45) Date of Patent: Feb. 26, 2002

(54) APPARATUS FOR ACOUSTICALLY DETERMINING POSITION OF AN ENDOTRACHEAL TUBE

(75) Inventor: Walter Dennis Clark, Fullerton, CA (US)

(73) Assignee: Integrated Medical Systems, Inc., Signal Hill, CA (US)

( * ) Notice: Subject to any disclaimer, the term of this patent is extended or adjusted under 35 U.S.C. 154(b) by 0 days.

(21) Appl. No.: 09/104,338

(22) Filed: Jun. 25, 1998

(51) Int. Cl.⁷ ............................................. A61M 16/00
(52) U.S. Cl. ........................... 128/200.26; 128/207.14; 128/205.23
(58) Field of Search ....................... 128/200.26, 207.14, 128/205.23

(56) References Cited

U.S. PATENT DOCUMENTS

| | | | | |
|---|---|---|---|---|
| 2,638,096 A | * | 5/1953 | Waldhaus | 128/207.14 |
| 2,904,033 A | * | 9/1959 | Shane | 128/205.23 |
| 3,848,605 A | | 11/1974 | Harautuneian et al. | 128/351 |
| 3,924,348 A | | 12/1975 | Taylor et al. | 46/17 |
| 4,344,436 A | | 8/1982 | Kubota | 128/350 |
| 4,416,289 A | | 11/1983 | Bresler | 128/737 |
| 4,431,005 A | | 2/1984 | McCormick | 128/656 |
| 4,445,501 A | * | 5/1984 | Bresler | 128/207.14 |
| 4,449,522 A | | 5/1984 | Baum | 128/200.26 |
| 4,567,882 A | * | 2/1986 | Heller | 128/200.26 |
| 4,630,606 A | | 12/1986 | Weerda | 128/207.14 |
| 4,633,864 A | | 1/1987 | Walsh | 128/207.15 |
| 4,840,172 A | | 6/1989 | Augustine et al. | 128/207.14 |
| 4,892,095 A | * | 1/1990 | Nakhgevany | 128/207.14 |
| 4,943,770 A | * | 7/1990 | Ashley-Rollman et al. | 128/207.14 |
| 5,005,572 A | | 4/1991 | Raemer et al. | 128/207.14 |
| 5,056,514 A | | 10/1991 | DuPont | 128/207.14 |
| 5,095,896 A | | 3/1992 | Omoigui | 128/200.26 |
| 5,197,464 A | | 3/1993 | Babb et al. | 128/207.14 |
| 5,257,636 A | | 11/1993 | White | 128/897 |
| 5,291,879 A | | 3/1994 | Babb et al. | 128/200.26 |
| 5,331,967 A | | 7/1994 | Akerson | 128/716 |
| 5,445,144 A | | 8/1995 | Wodicka et al. | 128/207.14 |
| 5,560,351 A | | 10/1996 | Gravenstein et al. | 128/200.26 |
| 5,562,078 A | * | 10/1996 | Dzwonkiewicz | 128/207.14 |
| 5,655,518 A | * | 8/1997 | Burden | 128/200.26 |
| 5,775,322 A | * | 7/1998 | Silverstein et al. | 128/200.26 |
| 5,785,051 A | * | 7/1998 | Lipscher et al. | 128/207.14 |
| 5,890,488 A | * | 4/1999 | Burden | 128/200.26 |

* cited by examiner

Primary Examiner—Aaron J. Lewis
(74) Attorney, Agent, or Firm—Stetina Brunda Garred & Brucker

(57) ABSTRACT

An endotracheal tube having an audio aid for indicating the accurate placement thereof. In a first preferred embodiment, the invention comprises a cuffed ETT having distal and proximal ends, the latter having a mechanical noise-making apparatus formed thereon that provides an audible signal when air passes therethrough. In a second preferred embodiment, the invention comprises the combination of a cuffed ETT having distal and proximal ends and an insertion rod for stiffening the ETT during insertion. The insertion rod is coupled to an electrically-powered noise maker formed upon the distal end thereof to produce an audible sound before air flow through the ETT is established. In both embodiments the correct placement is determined by the unaided ear hearing the noise coming from both sides of the chest. If sound is from one side only the insertion is too deep. If the sound is heard from the stomach the ETT is in the esophagus instead of trachea and should be pulled out and reinserted in such a way that it press more forcefully in the ventral direction.

11 Claims, 2 Drawing Sheets

APPARATUS FOR ACOUSTICALLY DETERMINING POSITION OF AN ENDOTRACHEAL TUBE

FIELD OF THE INVENTION

The present invention relates generally to endotracheal intubation devices, and more particularly, an endotracheal tube having an apparatus coupled therewith for acoustically indicating the placement of the distal end of the tube within a person's body to the unaided ear of a health care provider.

BACKGROUND OF THE INVENTION

Methods and apparatus for intubating the trachea of a patient are well-known in the art. In this regard, an endotracheal tube (hereinafter "ETT") is typically inserted through the mouth and into the trachea of a patient, and is ideally positioned such that the distal end thereof is placed just above the carina (i.e., the central ridge formed by the bifurcation of the trachea into the left and right bronchus). Introduction of the ETT into the body may alternatively be accomplished through nasotracheal intubation. In rare acute emergency situations, the ETT may be introduced directly into the trachea via tracheostomy or tracheotomy.

Ideally, endotracheal intubation via any of the aforementioned techniques should not be performed without the requisite tools, the minimum tool being a stethoscope, and experience to use the same. In this regard, endotracheal intubation may be complicated by inadvertent insertion of the ETT into the esophagus, or past the carina into one of the right primary bronchus or the left primary bronchus. Also, post placement movement of the distal ETT tip past either the carina or above the vocal cords due to patient or ventilator tube movement, or mucus blockage of the ETT lumen can occur over time. In all such scenarios, the patient is ineffectively ventilated which may result in severe medical complications, including death.

In an effort to avoid the aforementioned complications, techniques have been developed to aid clinicians in the determination of the location of ETT. Currently, clinical techniques utilized to evaluate ETT location include stethoscopic evaluation of the airway, breath, and epigastric sounds, respiratory system compliance measurements, detection of asymmetrical chest excursion, chest compression techniques, palpitation of the ETT cup over the extrathoratic trachea, electromagnetic detection devices, ultrasonic techniques, optical techniques, carbon-dioxide measurements, suctioning devices, and chest x-rays.

In addition to the aforementioned clinical techniques, there has been developed a variety of methods and apparatus for guiding and positioning ETTs within the body of a patient. Exemplary of such prior art devices include those disclosed in U.S. Pat. No. 5,445,144 to Wodicka, et al., which discloses an apparatus for acoustically guiding a distal end of a tube within a body which utilizes a waveguide coupled to the distal end of a tube with a speaker coupled therewith for generating an incident sound pulse in the waveguide which propagates into the body of the patient. A microphone coupled to the waveguide between the speaker and the tube is provided to detect sound pulses moving past the microphone and the waveguide from the incident sound pulse and from reflected sound pulses from within the body. Such system further includes means for processing the sound pulses detected by the microphone to guide insertion of the proximal end of the tube within the body. Other similar devices are disclosed in U.S. Pat. No. 5,560,351 to Gravenstein, et al.; U.S. Pat. No. 5,257,636 to White; U.S. Pat. No. 4,344,436 to Kubota; and U.S. Pat. No. 4,431,005 to McCormick.

In emergency situations occurring in remote locations, and particularly a battlefield, it is impractical for such aforementioned techniques to be performed. In this regard, the medical devices necessary to perform such techniques cannot be practically deployed in the context of a battlefield situation. Additionally, such clinical techniques necessarily must be performed by trained clinical personnel, which will likely be unavailable during such situations.

Ironically though, it is precisely those types of battlefield situations where endotracheal intubation must be performed to establish an emergency airway. Indeed, battlefield casualties can and frequently do experience occlusion of the airways or cessation of breathing, thus giving rise to a medical emergency. In this regard, after 4 to 5 minutes of anoxia, severe or irreversible brain damage is likely. Therefore, prompt establishment of a patent airway via an ETT is essential.

Accordingly, there is a need in the art for an ETT that may be easily and readily utilized to intubate the trachea of a casualty or other medical patient that can further provide an accurate indication of the placement of the distal end of the ETT within the body of the patient. There is additionally a need in the art for such an ETT that can provide an indication of the proper placement thereof by utilizing simple mechanical means which consequently does not rely upon any sophisticated equipment. There is still further a need in the art for an ETT that may be readily implemented by individuals having minimal training and/or experience in endotracheal intubation and ventilator operation.

SUMMARY OF THE INVENTION

The present invention specifically addresses and alleviates the aforementioned deficiencies in the art. Specifically, the present invention is directed to an audio aid for determining the optimum position of an ETT within a patient. According to a first preferred embodiment, the invention comprises a conventional cuffed ETT having distal and proximal ends; the proximal end is the part that remains outside the body. Formed upon the distal end is a mechanical noise maker, which may take the form of a reed, whistle or other like device. The ETT, and more particularly the distal end thereof, is advanced into the trachea or esophagus during endotracheal intubation. Once the distal end of the ETT has been sufficiently advanced such that an airway has been established, air will thus be drawn into and expelled from the ETT as the patient inhales and exhales. Such proper positioning will thus cause the mechanical noise-making device formed upon the distal end of the ETT to make audible sound to thus indicate to a caregiver that the ETT has been properly positioned within the trachea. Proper placement will be indicated by the sound being heard from both sides of the chest cavity equally and not from the stomach. This sound is heard with the unaided ear of the doctor, medic or nurse.

In a second preferred embodiment, the invention comprises the combination of a conventional cuffed ETT having distal and proximal ends and an insertion rod, the latter also having distal and proximal ends. The insertion rod further includes an electronic noise maker formed on the distal end thereof that produces an audible signal to assist the placement of the ETT within the trachea of a patient.

It is therefore an object of the present invention to provide an audio aid for the unaided ear to rapidly and properly position an ETT within a patient's trachea to provide a more intuitive aid in the proper positioning of the ETT than prior art systems.

Another object of the present invention is to provide an audio aid for properly positioning an ETT within a patient's trachea which can be used with conventional, inexpensive, readily available ETTs.

Another object of the present invention is to provide an audio aid for indicating the proper positioning of an ETT that provides an indication of the proper positioning of the ETT that further allows the patient to be simultaneously ventilated.

Another object of the present invention is to provide an audible aid for indicating the proper positioning of an ETT within a patient's trachea that provides a continuous audible indication as to the proper positioning of the ETT within the patient's trachea.

A still further object of the present invention is to provide an audible aid for indicating the proper positioning of an ETT within a patient's trachea that may be readily and easily used by a medic, or doctor with no special training in the operation of the device.

BRIEF DESCRIPTION OF THE DRAWINGS

These, as well as other features of the present invention, will become more apparent upon reference to the drawings, wherein.

DETAILED DESCRIPTION OF THE PREFERRED EMBODIMENT

The detailed description set forth below in connection with the appended drawings is intended merely as a description of the presently preferred embodiments of the invention, and is not intended to represent the only forms in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

Figure 1:
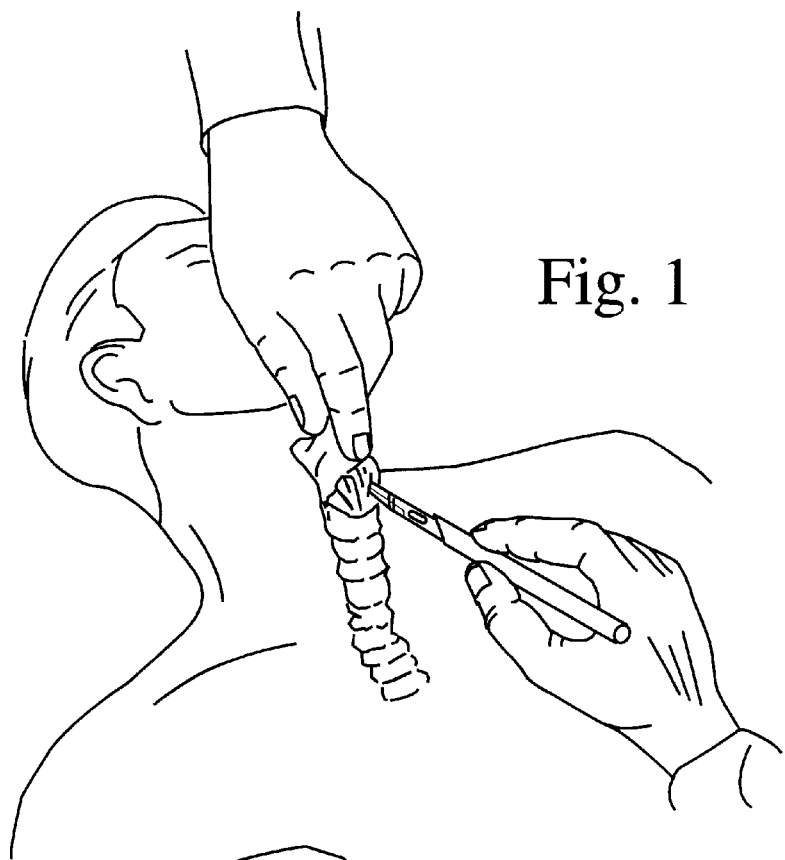
FIG. 1 is a perspective view of the head and neck region of a casualty undergoing tracheostomy.

Referring now to the Figures, and initially to FIG. 1, there is shown the head 12 and neck region 14 of an individual 10 undergoing an emergency tracheostomy. As frequently occurs with trauma victims, as well as patients experiencing cardiopulmonary arrest, respiratory failure, poisoning and/or drug overdose, the lumen of the trachea 16 can become closed off, thus blocking the flow of air from the lungs to the nose and/or mouth of the victim. In such situations, death or severe injury will result unless the obstruction is circumvented and the patient's airway reestablished.

In this regard, endotracheal intubation is indicated for all situations where free passage of air in and out of the lungs is endangered. Such procedure remains the quickest, most efficient and least traumatic technique for this purpose, which can arise either in the context of acute respiratory arrest, for example, severe head trauma with acute respiratory center paralysis and coma; penetrating chest trauma (as may be caused by bullets and shrapnel) with consequent anoxia; drowning or any other form of suffocation; acute and/or respiratory depression and apnea from drug overdose, or in chronic situations, for example, respiratory failure due to adult respiratory distress syndrome or acute exacerbation of chronic obstructive or restrictive lung disease.

Figure 2:
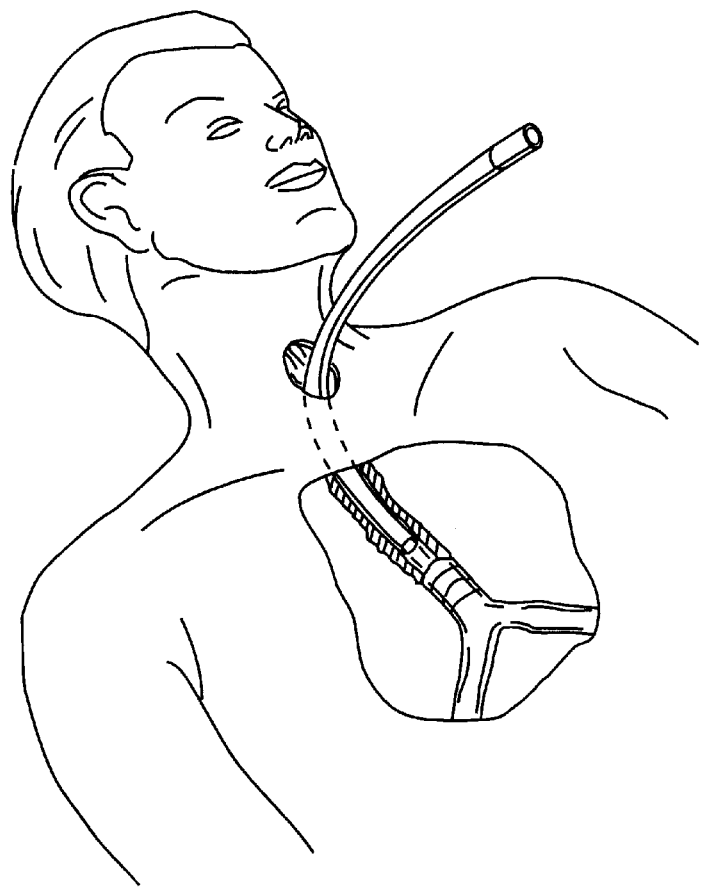
FIG. 2 is a perspective view of the head, neck and chest of the patient of FIG. 1 having an ETT constructed in accordance to a first preferred embodiment of the present invention shown positioned within the trachea thereof.

While it is well-known to those skilled in the practice that an airway can be established via oratracheal or nasotracheal intubation, the latter being preferable in emergencies, there is nonetheless depicted in FIG. 2 a third alternative, namely emergency circothyrotomy, which is warranted in cases where the patient has experienced severe facial trauma, or if the patient's clenched jaw obviates intubation. In such instances, which frequently occur in battlefield situations, the medic, who is typically an individual having minimal training, makes an incision over the trachea 16, as depicted in FIG. 1, and subsequently inserts an ETT into the trachea 16 until the life-saving airway is established.

As shown in FIG. 2, the ETT 18, and more particularly the distal end 18b thereof, is preferably positioned within the trachea 16 such that such distal end 18b remains resident below the vocal cords and just above the carina 20, i.e., the juncture between the trachea and the left and right bronchus 22, 24. To the extent the distal end 18b of the ETT 18 is inserted past the carina 20, ventilation will only be provided to either the right or left lung. As a consequence, the lung not ventilated by the ETT 18 will collapse and possibly cause the remaining lung to become damaged or fail to provide sufficient oxygen. Alternatively, if the ETT 18 is not inserted far enough into the trachea 16, it may not protect against aspiration of the patient's stomach contents or is more likely to be readily dislodged such that the air delivered therethrough may flow, in whole or in part, through the patient's mouth and/or nose and not adequately ventilate the lungs.

Figure 3A:
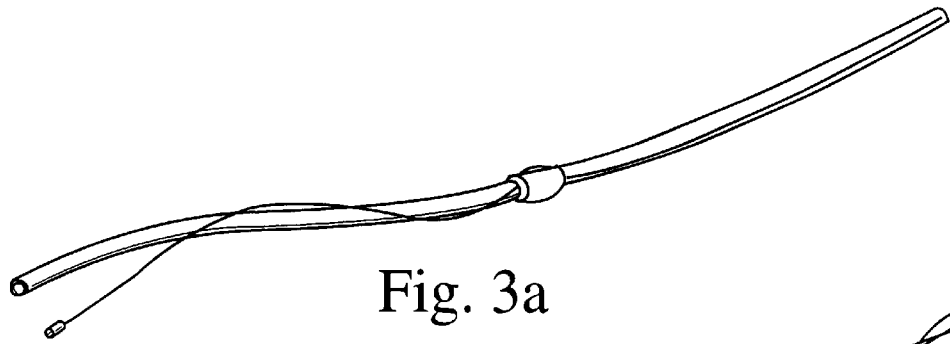
FIGS. 3A-C are perspective view of an ETT constructed in accordance to a second preferred embodiment of the present invention.
Figure 3B:
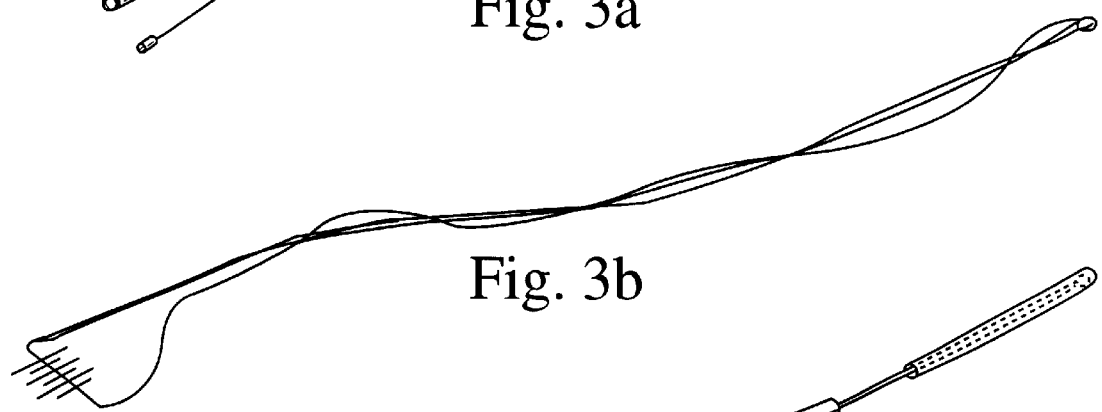
Figure 3C:
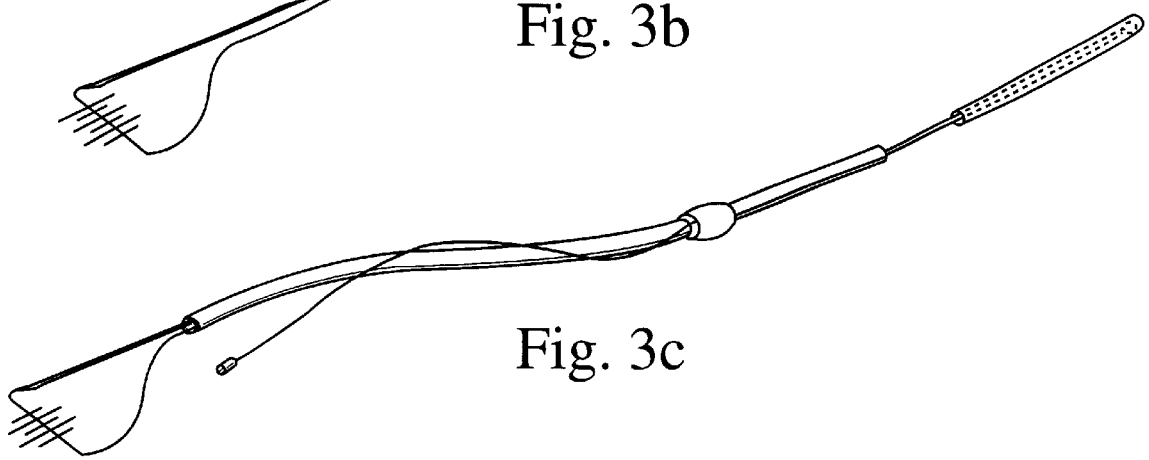

Referring now to FIGS. 3a–3c, there are depicted two (2) preferred embodiments of the present invention utilized to produce an audible signal for quickly and accurately indicating the proper position of the distal end of an ETT within the trachea of a patient. According to the first preferred embodiment 30 depicted in FIG. 3a, the invention comprises a conventional ETT 32 having distal and proximal ends 32a, 32b and an inflatable cuff 34 formed intermediate said ends. As is well-known to those skilled in the art, the distal end 32b of the ETT 32 is specifically designed and configured to be positioned within the trachea of a patient with the proximal end 32a thereof extending from the patient's body, whether nasally, orally or directly from the trachea itself, so that air may pass to and from the lungs without obstruction.

In order for the ETT 32 to be correctly operated, it is well-recognized that the distal end 32b thereof must be precisely positioned so that the tracheal cuff 34, which is necessary to provide an expandable or flexible sealing engagement with the trachea to thus tightly engage the ETT within the trachea. Should the tracheal cuff 34 be inserted too far down into the trachea, it will seal off either the right bronchus and/or the left bronchus, thereby preventing proper inflation of one or both lungs. As is well recognized, such tracheal cuff 34 is typically provided with means, such as manually operable pump 36, for inflating and deflating the same once positioned within the trachea.

Formed upon the distal end 32b of the ETT 32 is a mechanical noise maker 38, which may take the form of a reed, whistle, bell or any like device that can provide an audible signal when a current of air is passed therethrough or thereacross. The noise-making apparatus 38 may be formed as an integral part of the ETT 32 or, alternatively, may be detachably fastenable thereto. Such audible device 38 will thus produce an audible signal to aid in proper positioning of the ETT 32. Accordingly, once the audible sound is provided by the mechanical device 38, the caregiver positioning the tube will listen for that sound to come out through the chest indicating proper placement of the distal end 32b of the ETT 32 within the patient, thus alleviating the need for the use of a stethoscope to provide confirmation that the ETT 32 is properly positioned as is standard via conventional intubation methods. Furthermore, such audible signal will continue to be produced so long as the distal end 32b of the ETT 32 remains properly positioned within the patient.

Advantageously, to the extent the ETT 32 somehow deviates from its proper position, the audible signal will no longer be heard from the chest, thus immediately indicating the need for repositioning of the ETT 32 within the patient. Of further advantage is the fact that the audible device 38 is preferably of simple mechanical construction and, as a consequence, does not require the use of any type of sophisticated equipment requiring the need for a power source, such as batteries and the like. Such simple mechanical audio aid 38 further provides the benefit of simple and inexpensive construction. In this regard, because such audible device 38 does not employ any type of sophisticated equipment, the healthcare provider is thus not required to undergo special training as would be the case for any of the electronic sensor device for the same purpose.

Referring now to FIGS. 3b and 3c, there is shown a second preferred embodiment 40 of a system for indicating the proper placement of an ETT within the trachea of a patient. As shown in FIG. 3b, there is provided an elongate insertion rod or stylet 42 having distal and proximal ends 42a, 42b that is specifically designed and configured to facilitate the insertion and proper placement of an ETT 32, and more particularly the distal end 32b thereof, within the trachea of a patient. The insertion rod is provided with a noise making apparatus 44 formed on the distal-most end 42b thereof coupled, via a wire connection 46 or the like, to an external power source 48. The sensor 44 is designed to produce an audible signal even though no air is passing through the ETT.

As shown in FIG. 3c, the insertion rod 42 is designed and configured such that the distal end thereof 42b axially extends intraluminally through the ETT 32 as the same is inserted into a patient. In this regard, the insertion rod 42 actually facilitates the placement of the ETT 32 within the trachea of a patient by providing means for guiding the same into position, as well as providing stiffening means to thus enable the ETT 32, and more particularly the distal end 32b thereof, to properly advance within the trachea at the desired position.

Once the ETT and its insertion rod are properly positioned within the trachea, the insertion rod is removed to allow an open airway to be established that will cause air to flow both to and from the lungs.

Such insertion rod 42 may be designed to either be disposable or sterilizable for reuse. Advantageously, as with the first embodiment, the audio aid of the present invention according to the second embodiment uses relatively unsophisticated equipment that may be readily used with minimal training. Such embodiment further is of compact design and therefore space efficient, which thus enables the same to be readily transported and deployed in emergency situations, and in particular battlefield situations, where medics having minimal training will necessarily be required to quickly perform such intubation procedures under critical conditions.

Although the invention has been described herein with specific reference to a presently preferred embodiment thereof, it will be appreciated by those skilled in the art that various additions, modifications, deletions and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. An endotracheal tube having an audio aid formed thereon for producing an audible sound to the unaided ear to indicate accurate placement of the endotracheal tube within the trachea of a patient comprising:

a) an elongate, cuffed endotracheal tube having proximal and distal ends; and b) an audible sound-making apparatus formed upon the distal end of said endotracheal tube, said audible sound-making apparatus being operatively positionable intermediate the vocal chords and carina tracheas of said patient and designed and configured to produce an audible sound when said apparatus has a flow of air passing thorough the lumen of said endotracheal tube.

2. The device of claim 1 wherein said audible sound-making apparatus is designed and configured to produce an audible sound as air is expelled by said patient's lungs and through said endotracheal tube.

3. The device of claim 1 wherein said audible sound-making apparatus is designed and configured to produce an audible sound as air is inhaled into said patient's lungs and through said endotracheal tube.

4. The device of claim 1 wherein said audible sound-making apparatus is formed as an integral part of said endotracheal tube.

5. The device of claim 1 wherein said audible sound-making apparatus is detachably fastenable to either said proximal end or said distal end of said endotracheal tube, such that the sound emits from the distal end.

6. A system for determining that proper positioning of an ETT has been established prior to air flowing into the lungs of an individual comprising:

a) an elongate, cuffed endotracheal tube having distal and proximal ends; and b) an elongate insertion rod having proximal and distal ends axially extensible through said endotracheal tube for guiding said endotracheal tube into position said elongate insertion rod having an audible sensor formed thereon for producing sound to the unaided ear when operatively positioned within said endotracheal tube.

7. The system of claim 6 wherein said insertion rod is hollow and said audible sensor is formed upon the proximal end thereof, said audible sensor comprising an air-driven vibrating diaphragm wherein acoustic energy is conducted as sound from the proximal end, through the hollow insertion rod to emit at the distal end thereof.

8. The system of claim 6 wherein said audible sensor formed upon the insertion rod comprises an electrical sensor which is source and emitter at the distal end.

9. The system of claim 6 wherein said insertion rod and audible sensor formed thereon are formed from sterilizable material to enable the same to be reused.

10. The system of claim 6 wherein said insertion rod and audible sensor formed thereon are formed to be disposable.

11. The system of claim 6 wherein said insertion rod is hollow and said audible sensor is formed upon the distal end thereof, said audible sensor comprising an air-driven vibrating diaphragm operative to emit acoustic energy.

* * * * *